United States Patent [19]

Sinha et al.

[11] 4,383,171

[45] May 10, 1983

[54] PARTICLE ANALYZING METHOD AND APPARATUS

[75] Inventors: Mahadeva P. Sinha, Temple City; Charles E. Giffin, Pasadena; David D. Norris, San Gabriel; Sheldon K. Friedlander, Pasadena, all of Calif.

[73] Assignee: The United States of America as represented by the Administrator of the National Aeronautics and Space Administration, Washington, D.C.

[21] Appl. No.: 207,135

[22] Filed: Nov. 17, 1980

[51] Int. Cl.³ ............................................. B01D 59/44
[52] U.S. Cl. ................................... 250/282; 250/288; 250/423 P
[58] Field of Search ............ 250/281, 282, 288, 423 R, 250/423 P, 425

[56] References Cited

U.S. PATENT DOCUMENTS

| | | | |
|---|---|---|---|
| 3,436,966 | 4/1965 | Netusil et al. | 250/288 |
| 3,808,433 | 4/1974 | Fite et al. | 250/425 |
| 3,914,655 | 10/1975 | Dreyfus et al. | 250/423 P |
| 4,105,921 | 8/1978 | Bartlett | 250/423 P |
| 4,140,905 | 2/1979 | Polanyi | 250/423 P |

Primary Examiner—Bruce C. Anderson
Attorney, Agent, or Firm—Paul F. McCaul; John R. Manning; Thomas H. Jones

[57] ABSTRACT

A system is provided for analyzing the particles in aerosols, as in making air pollution studies, which enables the making of rapid chemical analyses of particles. The system includes an apparatus for producing a controlled stream of individual particles to be analyzed from an environment, and an apparatus for vaporizing and ionizing the particles while they move in free flight, for analysis by a mass spectrometer. The apparatus for producing a stream of particles includes a capillary tube through which the air with suspended particles moves, a skimmer device having a small opening spaced from an end of the capillary tube to receive particles passing through the tube, and a vacuum pump for pumping air out of the space between the tube and skimmer. The vacuum pump serves to remove much of the gas from around the particles, while also creating an inflow of air and particles through the capillary tube. The particles passing through the skimmer opening can be simultaneously vaporized and ionized while in free flight, by a laser beam of sufficient intensity that is directed across the path of the free flying particles.

12 Claims, 2 Drawing Figures

PARTICLE ANALYZING METHOD AND APPARATUS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; USC 2457).

BACKGROUND OF THE INVENTION

The analysis of aerosol particles, such as those causing air pollution, is typically performed by the use of cascaded-impact filters where particles are collected on a substrate for later laboratory analysis. One disadvantage of this technique is that there is considerable delay before the results are obtained. Another disadvantage is that large numbers of particles are analyzed together at the laboratory, so that the results only indicate the average properties of the particles. Additionally, considerable changes in the particles can occur between the time they are collected and the time they are analyzed, as the particles can react with each other and with the collecting substrate. A system which enabled the analysis of solid or liquid particles of an aerosol in real time, which enabled separate analysis of individual particles, and which avoided inaccuracies or lack of clarity resulting from the contact of particles with a substrate prior to analysis, would be of considerable value.

SUMMARY OF THE INVENTION

In accordance with one embodiment of the present invention, a system is provided for analyzing individual particles that may be originally contained in a gas such as air, which enables rapid and accurate analysis of the particles. The system includes an apparatus for passing particles along a predetermined path in free flight, so the particles are free of support from a substrate or the like. The system also includes an apparatus for vaporizing and ionizing the particles at a location along the path, and a mass spectrometer or other means for analyzing the ions generated from the particles.

An apparatus for passing the particles along a controlled path, includes a capillary tube having an entrance end positioned to receive the gas with suspended particles, and a skimmer having a small opening spaced from the exit end of the capillary tube. A vacuum pump evacuates the region between the capillary tube and skimmer, to simultaneously draw the gas with suspended particles in through the tube, and to minimize the amount of gas reaching the skimmer. The particles travel rapidly through the tube and through the evacuated region to reach the skimmer opening, so that the outlet of the skimmer provides a stream or beam of particles together with a greatly reduced amount of gas.

One apparatus for vaporizing and ionizing the particles includes an intense beam of electromagnetic radiation, such as from a laser, which rapidly heats the individual particles while they move in free flight. The laser beam is of an intensity to raise the particles to a temperature at which they not only vaporize, but wherein they produce ionized vapors. In another apparatus, the particles encounter a heated filament which vaporizes them, and a beam of charged particles such as electrons are directed at the vapors to ionize them.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
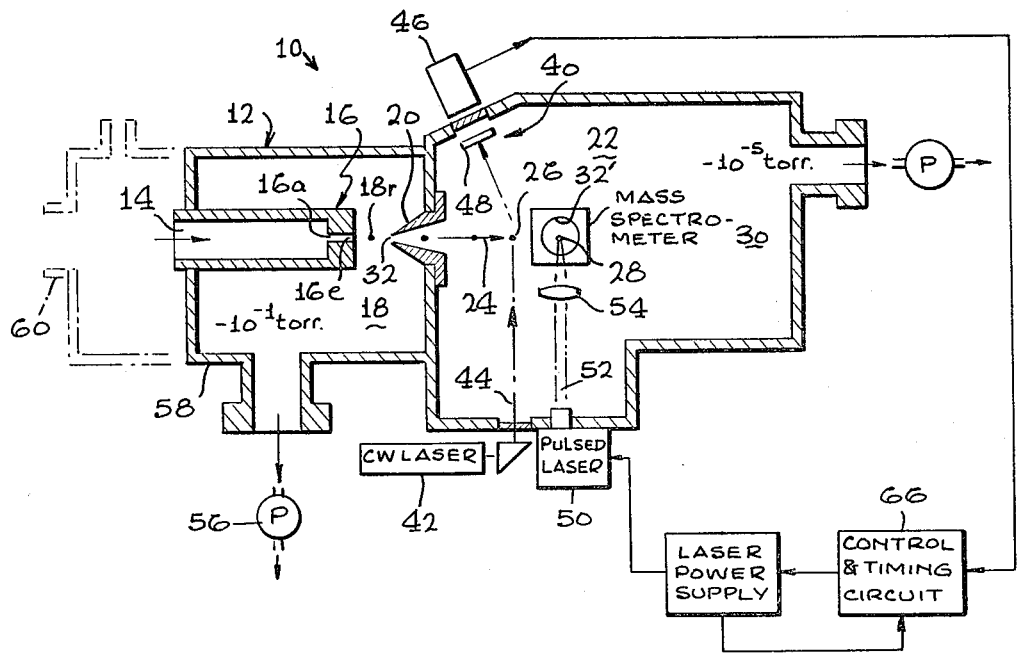
FIG. 1 is a simplified sectional view of a particle analyzing system constructed in accordance with the present invention.

FIG. 1 illustrates a particle analyzing system 10 which can be utilized to determine the composition of liquid or solid particles lying in a gas, as in air pollution monitoring. The apparatus is especially useful in analyzing aerosols which include particles on the order of one micron diameter which are dispersed in a gas such as air. The system 10 includes a particle control device 12 which has an opening 14 for receiving a gas containing the particles to be analyzed, such as an aerosol, and which delivers the aerosol to a capillary tube 16. The aerosol passes through the tube 16 into a separator chamber 18. The particles of the aerosol pass through the chamber 18 and through a skimmer 20 into an analyzing chamber 22. The particles move along a predetermined path 24, and the presence of each particle is detected at a location 26. Each particle continues to move along the path to a location 28 where it is vaporized and ionized. The ions derived from the particle are analyzed by an analyzing instrument such as a mass spectrometer 30 whose entrance 32' is located beside the path 24 of the particle.

The particle control device 12 which includes the capillary tube 16, separator chamber 18, and skimmer 20, is designed to create a beam of individual particles moving along a closely controlled path 24, and to deliver the particles along with a minimum of the gas in which the particles originally lay. The capillary tube 16 is narrow and long, so it controls the flow of the aerosol to confine the particles to move along a narrow path with minimum spread. An opening 32 in the skimmer is positioned in line with the path of the particles moving along the capillary tube 16, so to receive such particles. The separator chamber 18 which forms the region 18r between the tube and skimmer, is maintained at a lower pressure than the source from which the aerosol is received and which may be at atmospheric pressure. For example, the chamber 18 may be at a vacuum of $10^{-1}$ torr (i.e. about 1/8000th of an atmosphere). The low pressure in the chamber 18 serves to create a rapid flow of the aerosol through the capillary tube 16, to move the particles therethrough rapidly so that they pass across the chamber 18 into the skimmer opening 32. The low pressure in the chamber 18 also minimizes the amount of gas that will flow through the skimmer opening 32 into the analyzing chamber 22.

The reason why the particles in the aerosol easily pass across the chamber region 18r to the skimmer, while the gas in the aerosol does not, is due to the difference in the size and therefore the momentum, of the particles as compared to the gas molecules. The gas portion of the aerosol which leaves the exit end 16e of the capillary tube, expands into a free jet and most of it is pumped out and does not reach the skimmer opening. The particles, being much heavier, have less divergence and pass through the skimmer opening 32. Thus, the skimmer functions as a particle-air separator, which reduces the pumping load on the diffusion pump connected to the mass spectrometer analyzing chamber 22.

The arrival of each particle at the detection location 26 is sensed by a detector apparatus 40 which includes a laser 42 which directs a continuous narrow beam of light 44 across the path of the particles. A particle at the location 26 scatters the beam, so that some of the light reaches a photomultiplier tube 46 whose photosensitive surface is covered by an interference filter 48. After a particle is detected at the location 26, a more powerful laser 50 is energized. The laser 50 directs a beam 52 through a lens 54 which concentrates the light, to produce a narrow but intense beam at the analyzing location 28 along the particle path. The beam intensity is great enough to raise the temperature of the particle to a high level, which is considerably above the temperature needed to vaporize the particle. The temperature is high enough that ionized vapor molecules are created. The ionized molecules derived from the particle, are created at a location adjacent to the entrance of the mass spectrometer 30. The ions are drawn into the mass spectrometer and are analyzed by it. A mass spectrometer of the type described in U.S. Pat. No. 3,955,084 entitled "Electro-Optical Detector for Use in a Wide Mass Range Mass-Spectrometer" by Charles E. Giffen, may be utilized to analyze the ions produced from the particle.

The vaporization and ionization of a particle by a laser beam, while the particle is in free flight (free of support by a liquid or solid substrate) enables the generation and detection of substantially only those ions which represent the particle. The fact that the particle is in free flight, and is surrounded only by gas at low pressure, results in the absence of vaporization of any substrate or the like that has been utilized in the prior art to hold particles. Laser vaporization and ionization is advantageous because it is "gentle" in that it tends to avoid the break-up of molecules originally present in the particle into many smaller particles, which would complicate the analysis. Electromagnetic radiation has been utilized to vaporize and ionize particles after they have been collected on a substrate. However, the application of a laser beam or the like to a particle on such a substrate can lead to vaporization and ionization of a portion of the substrate, which affects the analysis. In addition, the particles can react with one another and with the substrate prior to analysis, to create species that are not present in the original particle, and the collection on a substrate results in considerable effort and delay before analysis can be made. The application of a beam of optical radiation to particles in free flight, enables an analysis to be made in real time, and with minimal degradation of ions that represent the parent molecules present in the particles of the original aerosol.

In one particle analyzing system, for analyzing particles of about one micron diameter, the capillary tube 16 has an inside diameter of about 100 microns and a length of about 5 millimeters between its entrance and exit ends 16a, 16e. The skimmer 20 was formed as a cone with an opening 32 of 400 microns diameter and positioned in alignment with the capillary tube. The region 18r between the skimmer opening 32 and the exit end 16e of the capillary tube was about 3 millimeters long, and the chamber which includes this region was evacuated to a pressure of about 1/10th torr by the use of a pump 56 connected to a housing 58 which forms the chamber 18. When the system opening 14 was opened to atmospheric pressure, the particles passed through the skimmer 20 with a typical velocity of about 200 meters per second. The apparatus can be tested by utilizing a particle generator connected to an entrance 60 at a calibration source, to introduce particles of known composition and size through the inlet 14 of the apparatus.

In one system for analyzing particles of about one micron diameter, the laser 50 generates a beam having a width at the analyzing location 28 of about 50 to 100 microns diameter and having an intensity of about $10^8$ to $10^9$ watts per square centimeter. The laser 50 produces about one joule energy per pulse, and the pulse lasts for about 120 microseconds. Although the laser pulse lasts for about 120 microseconds, it is "seen" by the particle for only a fraction of that time, such as about 0.5 microsecond. A plume of ionized vapor is then generated from the particle. Thus, the laser is on for a much longer period than required to vaporize and ionize the particle. The period of time such as 120 microseconds, and the width of the laser beam such as 100 microns, is chosen to assure that the particle will be "hit" by the laser pulse. The use of a pulsed laser enables high energy laser beams to be generated with a laser of moderate size.

In the system of FIG. 1, the laser is pulsed on after each detection of a particle by the photomultiplier 46. The pulse produced by the photomultiplier 46 is delivered to a control and timing circuit 66 which triggers the pulsed laser 50, so that the laser 50 delivers its pulse at a predetermined time after the particle is detected at the location 26.

Figure 2:
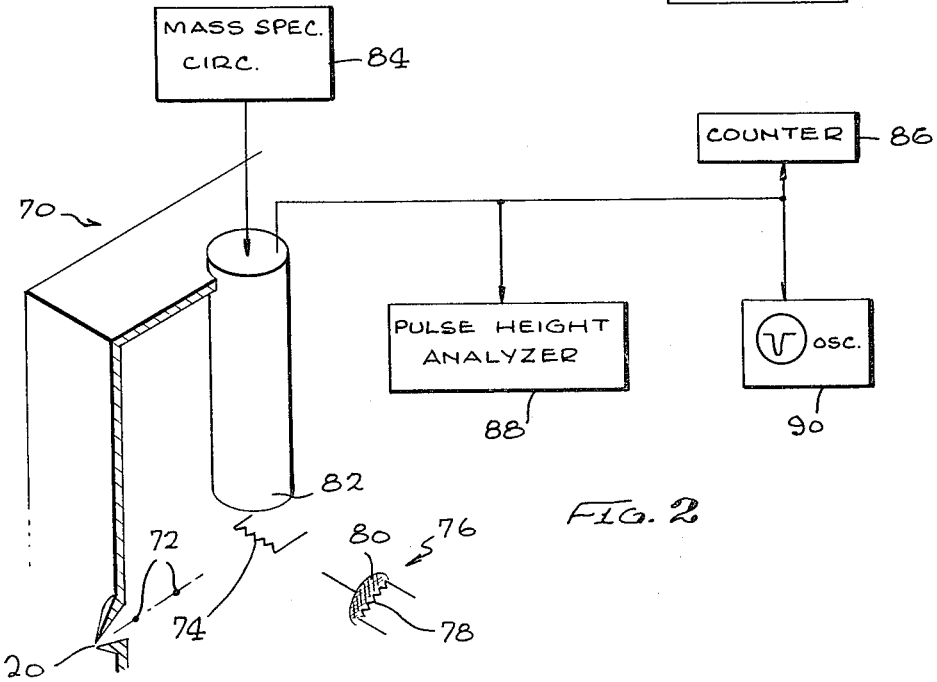
FIG. 2 is a partial perspective view of an analyzing system constructed in accordance with another embodiment of the invention.

FIG. 2 illustrates another particle analyzing system 70 which can be utilized to vaporize and ionize particles moving in free flight. The apparatus 70 includes a particle control device such as that shown at 12 in FIG. 1, to produce a stream of particles through a skimmer 20. As shown in FIG. 2, the particle such as 72 moves along a path to a heated body such as filament 74 which vaporizes the particle. A rhenium filament has been utilized which has been heated to a temperature such as 250° C. to 1200° C., to vaporize the particles. The ionization of the particles is performed by a conventional electron source 76 which includes a filament 78 heated to a temperature such as 2500° C. to boil off electrons that are accelerated towards the region of the vapors produced at the filament 74, as by a positive electrode 80. The electrons strike the molecules resulting from vaporizing the particle, the ionize the molecules. The ionized molecules are then analyzed by a mass spectrometer 82 which includes a quadrupole mass filter. The circuitry utilized with the spectrometer 82 includes a mass spectrometer energizing and control circuit 84, and circuits for receiving the output pulses generated by the spectrometer upon its detection of ions. This later circuitry includes a counter 86 which counts the number of particles that have been detected, and a pulse height analyzer 88 which measures the total number of ions in each particle. The pulse can be displayed on an oscilloscope 90. It has been found that in utilizing the device of FIG. 2, that ions bursts are produced which are each of about 80 to 100 microseconds pulse width, and that the apparatus has been useful in analyzing a variety of particles including sodium sulfite, ammonium sulfate lithium nitrate, adipic acid, glutaric acid, dioctyl phthalate, and some amino acids.

Thus, the invention provides an apparatus and method for analyzing particles, which enables accurate analyses to be performed in minimal time. The apparatus includes a device for passing particles along a predetermined path, free of support from a substrate or the like, an apparatus for vaporizing and ionizing the particles while they move in free flight along the path, and a device for detecting the ions generated from the vaporized particles. The apparatus for passing the particles along a predetermined path, can include a narrow, long tube for directing the particles along with the surrounding gas in a narrow path, and a skimmer having a narrow opening aligned with the narrow tube but spaced from it, so that most of the particles can pass through the region between the tube and skimmer while a much smaller percentage of gas molecules can pass therethrough. The region between the capillary tube and skimmer can be maintained at a vacuum, to draw in the gas and particles so they move rapidly through the capillary tube, while also minimizing the amount of gas which passes through the opening of the skimmer.

What is claimed is:

1. Apparatus for analyzing liquid or solid particles comprising:
   means for passing individual particles to be analyzed that each have a mass that is a plurality of orders of magnitude greater than the mass of molecules in air, in free flight past a predetermined path location;
   means for directing a light beam across said location, with an intensity to heat a particle sufficiently to vaporize and ionize it; and
   mass spectrometer means located near said path location for analyzing the ions resulting from the particle vaporization and ionization.

2. The apparatus described in claim 1 including:
   means for directing particles rapidly along a path which includes said path location; and
   means for detecting the presence of a particle at a position upstream from said path location; and wherein
   said means for directing a light beam includes means responsive to the detection of a particle by said detecting means, for generating a light pulse at a time after said detecting means detects a particle.

3. A method for analyzing solid or liquid particles in a gas stream of gas molecules, where the particles each have a mass which is orders of magnitude greater than that of said gas molecules, comprising:
   passing said particles along a predetermined path free of support from a substrate;
   applying electromagnetic radiation to at least one particle while it passes along said path, at an intensity high enough to vaporize and ionize it; and
   detecting the ions generated from the vaporized particle.

4. The method described in claim 3 including:
   detecting individual particles passing a predetermined location along said path, and applying said radiation in a brief pulse to the detected particle upon its detection.

5. A method for analyzing solid or liquid particles in a gas stream, where each particle has a mass that is a plurality of orders of magnitude greater than the mass of each gas molecule comprising:
   passing said particles along a predetermined path free of support from a substrate, to a heated body which is hot enough to vaporize the particle;
   directing a stream of ionizing electrons at the vapor to ionize it; and
   detecting the resulting ions.

6. The method described in claim 5 including:
   detecting individual particles passing a predetermined location along said path, and applying said radiation in a brief pulse to the detected particle upon its detection.

7. Apparatus for analyzing solid or liquid particles generally on the order of one micron diameter, that are entrained in a gas, comprising:
   means for passing said particles in free flight along a predetermined path;
   means for vaporizing and ionizing at least one of said particles while it passes along said path, including means for applying electromagnetic radiation of an intensity to vaporize the particle while it remains in free flight; and
   means for detecting the ions generated from the vaporized particle.

8. The apparatus described in claim 7 wherien:
   said means for applying radiation applies radiation of an intensity on the order of $10^9$ watts per square centimeter.

9. The apparatus described in claim 7 including:
   means for detecting the presence of a particle at a location along said path, and means responsive to said detecting means for operating said radiation applying means to deliver a pulse of optical radiation.

10. Apparatus for analyzing solid or liquid particles generally on the order of one micron diameter, that are entrained in a gas, comprising:
    means for passing said particles in free flight along a predetermined path;
    means for vaporizing and ionizing at least one of said particles while it passes along said path, including a heated body located along said path for vaporizing said particles, and an electron source aimed to apply electrons to a location near said heated body to ionize the vapor; and
    means for detecting the ions generated from the vaporized particle.

11. In apparatus for analyzing particles entrained in a gas, wherein the particles each have a mass which is orders of magnitude greater than the mass of each of the molecules of said gas, the improvement of means for providing a stream of particles, comprising:
    a narrow tube having a length which is a plurality of times greater than its inside diameter, said tube having an entrance end for receiving gas with particles entrained therein, and an exit end;
    a skimmer having a narrow opening spaced from but aligned with said narrow tube, to receive particles moving in a largely straight path from said tube to said skimmer;
    a housing surrounding the region between said narrow tube and said skimmer, and forming said region with a cross-section much larger than the cross-section of said tube, to permit the dispersion of gas therein to minimize the amount of gas reaching said skimmer opening;
    means for evacuating gas from said region; and
    means for applying optical radiation to a path location which lies beyond an end of said skimmer which is opposite said tube, in an intensity to ionize and vaporize free particles moving past said path location, and means for detecting the resulting ions.

12. In apparatus for analyzing particles entrained in a gas, wherein the particles each have a mass which is orders of magnitude greater than the mass of each of the molecules of said gas, the improvement of means for providing a stream of particles, comprising:

a narrow tube having a length which is a plurality of times greater than its inside diameter, said tube having an entrance end for receiving gas with particles entrained therein, and an exit end;

a skimmer having a narrow opening spaced from but aligned with said narrow tube, to receive particles moving in a largely straight path from said tube to said skimmer;

a housing surrounding the region between said narrow tube and said skimmer, and forming said region with a cross-section much larger than the cross-section of said tube, to permit the dispersion of gas therein to minimize the amount of gas reaching said skimmer opening;

means for evacuating gas from said region; and means for applying sufficient heat to particles moving past a path location beyond an end of said skimmer which is opposite said tube, to vaporize the particles, and means for applying an electron stream to a location at least near said path location to ionize the vapor.

* * * * *